(12) United States Patent
Panza et al.

(10) Patent No.: US 9,422,212 B2
(45) Date of Patent: Aug. 23, 2016

(54) RECOVERY OF $CO_2$ IN A PROCESS FOR THE SYNTHESIS OF METHANOL

(71) Applicant: Casale SA, Lugano (CH)

(72) Inventors: Sergio Panza, Como (IT); Giovanni Luigi Capetti, Lugano (CH)

(73) Assignee: Casale SA (CH)

( * ) Notice: Subject to any disclaimer, the term of this patent is extended or adjusted under 35 U.S.C. 154(b) by 0 days.

(21) Appl. No.: 14/658,902

(22) Filed: Mar. 16, 2015

(65) Prior Publication Data

US 2015/0251983 A1    Sep. 10, 2015

Related U.S. Application Data

(63) Continuation of application No. 13/201,556, filed as application No. PCT/EP2010/052893 on Mar. 8, 2010, now abandoned.

(30) Foreign Application Priority Data

Mar. 13, 2009   (EP) .................................... 09155137

(51) Int. Cl.
*C07C 27/00* (2006.01)
*C07C 29/151* (2006.01)
*C01B 3/34* (2006.01)
*C01B 3/50* (2006.01)
*B01J 19/24* (2006.01)
*C01B 3/38* (2006.01)

(52) U.S. Cl.
CPC .......... *C07C 29/1518* (2013.01); *B01J 19/245* (2013.01); *C01B 3/34* (2013.01); *C01B 3/38* (2013.01); *C01B 3/50* (2013.01); *B01J 2219/24* (2013.01); *C01B 2203/0233* (2013.01); *C01B 2203/0238* (2013.01); *C01B 2203/048* (2013.01); *C01B 2203/061* (2013.01); *C01B 2203/1241* (2013.01); *C01B 2203/1282* (2013.01); *C01B 2203/148* (2013.01); *Y10T 29/49716* (2015.01)

(58) Field of Classification Search
CPC ..... C07C 29/1518; C07C 31/04; C01B 3/34; C01B 3/50; C01B 2203/2203; C01B 2203/048; C01B 2203/061; C01B 2203/148; C01B 2203/1241; C10G 2/32
USPC .......................................... 518/700, 702–705
See application file for complete search history.

(56) References Cited

U.S. PATENT DOCUMENTS

| | | | |
|---|---|---|---|
| 6,191,174 B1 * | 2/2001 | Early ................. | C07C 29/1518 422/236 |
| 2003/0092945 A1* | 5/2003 | Seiki ................... | C07C 29/1518 568/700 |
| 2008/0039652 A1* | 2/2008 | Thiebaut ............. | C07C 29/1518 562/512 |

FOREIGN PATENT DOCUMENTS

CN          1341586 A          3/2002

*Primary Examiner* — Jafar Parsa
(74) *Attorney, Agent, or Firm* — Akerman LLP (57) ABSTRACT

A process for producing methanol, where a hydrocarbon feedstock (1) is reformed and a make-up syngas is reacted in a synthesis loop, obtaining crude methanol which is further treated to obtain high-grade methanol, and where the carbon dioxide dissolved in the crude methanol is recycled to the reforming section in order to adjust the stoichiometric number of the make-up syngas. In a preferred embodiment, a flash gas (9) separated from the crude methanol (8) and light ends (10) coming from distillation are recycled to a compressor (106) and fed to a primary reformer (100); further carbon dioxide can be recycled from the flue gas (11).

7 Claims, 2 Drawing Sheets (51) Int. Cl.

RECOVERY OF $CO_2$ IN A PROCESS FOR THE SYNTHESIS OF METHANOL

CROSS-REFERENCE TO RELATED APPLICATIONS

This application is a continuation of U.S. patent application Ser. No. 13/201,556, filed Aug. 15, 2011, which is a national phase of PCT/EP2010/052893, filed Mar. 8, 2010, which claims priority to European Patent Application No. 09155137.4 filed Mar. 13, 2009, the disclosures of which are hereby incorporated by reference in their entirety.

FIELD OF THE INVENTION

The invention relates to synthesis of methanol from reforming of a hydrocarbon feedstock.

PRIOR ART

A large number of methanol (MeOH) plants in the world operate with a synthesis gas produced by steam reforming of a hydrocarbon feedstock, usually a light hydrocarbon such as natural gas. The steam reforming yields a make-up synthesis gas mainly comprising carbon oxides (CO, $CO_2$) and hydrogen ($H_2$), which is reacted in a high-pressure synthesis loop to produce methanol. The source of hydrocarbon can be any hydrocarbon or mixture thereof; a common example is natural gas.

A prior art process is based on the following steps: the feed gas, for example natural gas, is de-sulphurized and steam-reformed, producing a hot syngas usually at a pressure of around 20-40 bar; the syngas is cooled to recover heat, and fed to a main syngas compressor to raise the pressure at the operating value of the synthesis loop (usually 100 bar or more); the syngas is then reacted in said loop, obtaining a so-called crude methanol; the crude methanol is then treated in a distillation section in order to reach the required purity.

The steam-reforming can be performed with different configurations: non-limitative examples are: a stand-alone primary reformer; a primary reformer followed by a secondary reformer, possibly an auto-thermal reformer; a stand-alone auto-thermal reformer.

The reactions in the synthesis loop can be summarized as:

$$CO + 2H_2 \rightarrow CH_3OH \quad (I)$$

$$CO_2 + 3H_2 \rightarrow CH_3OH + H_2O \quad (II)$$

The reactants CO, $CO_2$ and $H_2$ are supplied by the make-up syngas. It can be understood from the above reactions that the concentration of carbon oxides (CO and $CO_2$) and hydrogen of the make-up syngas is crucial. The molar hydrogen-to-carbon ratio of the syngas produced in the reforming process is usually defined by the stoichiometric number R:

$$R = \frac{[H_2] - [CO_2]}{[CO] + [CO_2]}$$

The thermodynamic correct value of R is 2; it is known however that the kinetic of the reactions in the high-pressure (HP) synthesis loop asks for an optimum R slightly greater than 2, preferably in the range 2.05 to 2.3, depending on the $CO/CO_2$ ratio. A higher or lower R of the syngas means that the HP loop operates under its capability.

The syngas delivered by the reformer(s) can significantly deviate from said optimum value of R, so there is the need to adjust the stoichiometric number to the optimum value close to 2.

Known measures to adjust the value of R are: the recycling of hydrogen from the synthesis loop purge gas, based on membranes or on pressure swing adsorption (PSA) devices, and the recycling of carbon dioxide contained in the flue gas from the steam reforming process. Recycling a $H_2$— or $CO_2$-containing stream helps respectively to increase, or to lower, the value of R.

For example, a process based on auto-thermal reforming typically produces a syngas with carbon oxides in excess (R<2); in this case recovering hydrogen from the HP loop purge gas and adding recovered hydrogen to the make-up syngas helps to adjust (i.e. increase) the value of R. On the contrary, a primary reformer produces a hydrogen-rich syngas and, in this case, the stoichiometric number R is balanced by recovering carbon dioxide from the flue gas of the reformer itself.

Recovering the carbon dioxide contained in the flue gas is however expensive. A conventional $CO_2$-recovery section for this purpose is made basically with an absorber tower where the flue gas are counter-currently washed with a suitable solution, e.g. an amine-based solution; a $CO_2$-rich solution is separated at the bottom of the tower and is purified in a regenerator, where reboilers supply heat to the solution in order to break the bound between the solution and the carbon dioxide; a $CO_2$-rich gaseus stream is separated at the top of the regenerator, compressed in a suitable compressor and recycled back to the primary reformer.

This recovery section is normally very expensive and consumes a lot of energy. A substantial amount of energy, in fact, is required to separate the carbon dioxide from the rest of the flue gas components. The economical impact of this technique of $CO_2$ recovery on the whole process is not negligible.

The majority of the existing MeOH plants, and many of the new plants, are based on steam reforming of the feed gas charge with a primary reformer and, then, suffer the problem of hydrogen excess in the make-up syngas. The reforming process of these plants usually delivers a make-up syngas with R>3. As above, the recover of the carbon dioxide contained in the flue gas can help to solve this problem but is quite expensive, both in terms of capital cost and energy consumption. Hence, there is the need to find a less expensive way to balance the reactants of the make-up syngas close to the optimum value for the downstream synthesis loop.

Figure 3:
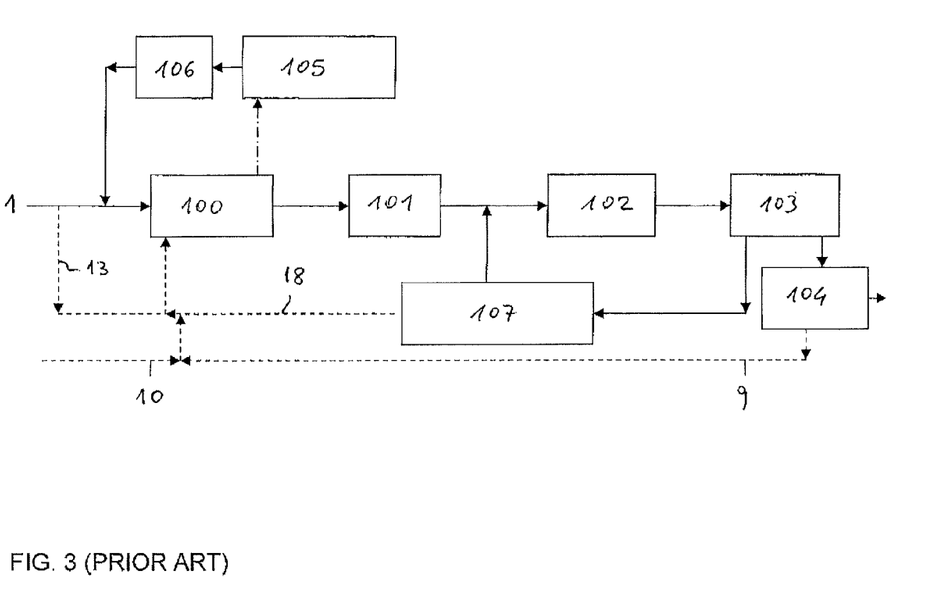
FIG. 3 is a simplified layout of a prior art methanol plant.

FIG. 3 is a simplified layout of a prior-art methanol plant, comprising a reformer 100, a synthesis loop 103, a $CO_2$ recovery section 105 and a hydrogen recovery section 107. Crude methanol produced in the loop 103 is de-gassed in a flash gas separator 104. Carbon dioxide is recovered from the flue gas of the reformer 100 and recycled to the same reformer, via a $CO_2$ compressor 106.

The flash gas 9 from said separator 104 and light ends 10 released from distillation of crude methanol are recycled as fuel to the primary reformer 100, together with a portion 13 of the feed 1, and a stream 18 from the hydrogen recovery section 107.

SUMMARY OF INVENTION

In a process for synthesis of methanol, the technical problem faced by the invention is to provide a simple and inexpensive method for adjusting the content of carbon oxides and hydrogen in the make-up syngas, in particular in a hydrogen-rich make up syngas.

The basic idea underlying the invention is to recover the carbon dioxide dissolved in the crude methanol. It has been found that this carbon dioxide can be recovered with relatively inexpensive equipments, compared to the recovery from the flue gas of a reformer. Hence, the invention makes available a cost-effective $CO_2$ rich stream that can be used to balance, at least partially, the stoichiometric number R of the make-up syngas.

In accordance with the invention, the above technical problem is solved with a process for producing methanol, comprising the steps of:
a. reforming a hydrocarbon feedstock in a reforming process step, obtaining a make-up syngas comprising carbon oxides and hydrogen;
b. reacting said make-up syngas in a methanol synthesis loop, obtaining crude methanol;
c. processing said crude methanol to obtain methanol of a required purity;
characterized by the steps of:
d. recovering at least one $CO_2$-containing stream from the processing of said crude methanol, and
e. recycling said at least one $CO_2$-containing stream as an input stream for said reforming process step.

The term "$CO_2$-containing stream" is used in this specification to mean a stream containing carbon oxides, mainly carbon dioxide $CO_2$. The term $CO_2$ stream will also be used with the same meaning.

In preferred aspects of the invention, the step of recovering a $CO_2$-containing stream from crude methanol is performed with at least one of the following techniques, and preferably with both the following techniques:
recovering a flash gas stream released by de-pressurization of the crude methanol produced in the synthesis loop;
recovering a gas stream containing carbon dioxide released by distillation of the crude methanol.

The flash gas stream released by de-pressurization of the crude methanol has a relevant content of $CO_2$, due to high solubility of the $CO_2$ in the methanol. The gas stream released in the distillation process is usually referred to as "light ends". The light ends are commonly released from the top of the first column (topping column) of a distillation section, and they are also rich of carbon dioxide.

Said flash gas stream and said light-ends stream, in one embodiment of the invention, are mixed together forming a single $CO_2$-containing flow, which is recycled to the reforming section, being the input stream of the process step e) as listed above.

The invention is also applicable to a process including the conventional carbon-dioxide recovery from the flue gas of a reformer. In some embodiments of the invention, the disclosed recovery of carbon dioxide from crude methanol is used in combination with the recovery from the flue gas of the reformer(s); in other embodiments, the recover from crude methanol can be the only recover of carbon dioxide The recovered $CO_2$-containing stream can be fed directly or indirectly to the reforming process. In a preferred embodiment, said $CO_2$-containing stream is compressed in a suitable $CO_2$ compressor and mixed with the hydrocarbon feedstock, at the inlet of a reformer of the reforming section. Said reformer can be an autothermal reformer or a primary reformer, such as a catalytic tube reformer, possibly followed by a secondary reformer.

The invention is applicable preferably, but not exclusively, to process and plants with a stand-alone primary reformer producing a syngas with a significant hydrogen excess, e.g. with the stoichiometric number R around 3, or even greater; the recover of carbon dioxide dissolved in the crude methanol, and its recycle to the reformer, helps to adjust the stoichiometric number at the correct value close to 2.

The main advantage of the inventive process is that at least part of the carbon dioxide is recovered in a much less expensive way, if compared to the known separation from the flue gas of the reformer. It should be noted that the flash gas and light ends are used as fuels or discharged in the prior art, while the invention provides their more effective use as process streams. The recycle of said streams allows gives a better low heating value (LHV) of the fuel gas used in the plant, achieving a better efficiency of the primary reformer. This better efficiency of the primary reformer can be explained with a higher pre-heating temperature achievable in the reformer coils, and with a lower temperature and flue gas flow rate at reformer stack. A higher efficiency of the primary reformer means also lower pollutant emissions in the atmosphere.

Referring now to embodiments featuring the carbon dioxide recovery from the reformer flue gas, the further $CO_2$-containing stream recovered from crude methanol, e.g. from flash gas and/or light ends, is fed to a carbon dioxide compressor, downstream a recovery section operating on said reformer flue gas. The gas recycle at the suction of the $CO_2$ compressor reduces the overall carbon dioxide required from the energy-intensive process of $CO_2$ recovery from the flue gas, thus resulting in significant energy savings for the whole process.

In summary, the recycle of carbon oxides (mainly $CO_2$) at the suction of the $CO_2$ compressor allows to achieve the following benefits/advantages: the reduction of the cost and energy consumption of the conventional $CO_2$ recovery section (when provided); improved energy efficiency of the plant and specifically of the primary reformer; reduced pollutant emissions.

It should be noted that carbon dioxide is a reactant in the synthesis loop, hence the recycle of the carbon dioxide dissolved in the crude methanol is also positive for the synthesis loop.

f appropriate, the process may also include hydrogen recovery from synthesis loop purge gas. The $H_2$-rich stream so obtained is preferably injected upstream the main syngas compressor.

The invention also relates to a plant for carrying out the above process. In particular, the invention relates to a plant for producing methanol comprising: a reforming section receiving a hydrocarbon feedstock, and producing a reformed make-up syngas comprising carbon oxides and hydrogen; a methanol synthesis loop, fed with the make-up syngas and producing crude methanol; a section where said crude methanol is processed to obtain methanol of a required purity; the plant being characterized by:
means for recovering at least one $CO_2$-containing stream separated from the processing of said crude methanol, and
means feeding said at least one $CO_2$-containing stream to said reforming section.

Preferably, the plant comprises a flash gas separator where a flash gas containing $CO_2$ is obtained from de-pressurization of crude methanol. The means for recovering said flash gas and feeding it to reforming section comprise a piping feeding the flash to the inlet of a $CO_2$ compressor, and feeding the delivery of said compressor at the inlet of the reforming section. Said means can also comprise a piping adapted to recover the light-ends gas stream released in a distillation section of crude methanol.

Another object of the invention is a method for revamping of an existing plant. Hence, one aspect of the invention is a method for revamping a methanol plant, said plant comprising at least a reforming section receiving a hydrocarbon feedstock, and producing a make-up syngas comprising carbon oxides and hydrogen, a methanol synthesis loop fed with the make-up syngas and producing crude methanol, and a section where said crude methanol is treated to obtain substantially pure methanol, the method being characterized by the provision of at least:

means for recovering at least one $CO_2$-containing stream separated from said crude methanol, and means feeding said $CO_2$-containing stream to said reforming section.

A first application of the inventive method involves that, in a plant for producing methanol with a conventional $CO_2$-recovery section, the flash gas and/or the light ends are recovered and fed to the inlet of said existing $CO_2$ compressor. In this case, the energy consumed by the flue gas $CO_2$-recovery section is decreased, as a less expensive $CO_2$ feed is available from the flash gas and light ends stream. A second application involves that, in a plant with no $CO_2$ recovery, a new compressor for the carbon dioxide is installed. As apparent for a skilled person, the revamping will also involve the provision of necessary equipment and auxiliaries such as piping, valves, etc. . . . .

The advantages of the invention will be more evident with the following detailed description of a preferred embodiment, presented as a non-limitative example.

DETAILED DESCRIPTION OF PREFERRED EMBODIMENTS

Figure 1:
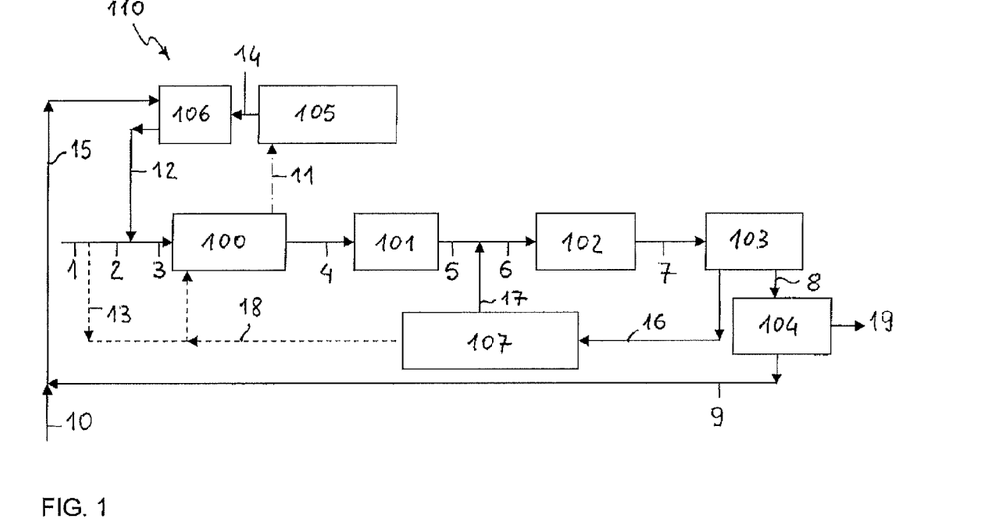
FIG. 1 is a simplified block diagram of a methanol plant according to one embodiment of the invention, and including the recovery of carbon dioxide from the flue gas of a primary reformer.

The plant of FIG. 1 comprises basically a primary reformer 100, a gas cooler 101, a syngas compressor 102, a methanol synthesis loop 103. The primary reformer 100 is part of a reforming section 110, comprising also a $CO_2$ recovery section 105 and a $CO_2$ compressor 106.

The primary reformer 100 is for example a catalytic tube reactor, according to well known art. All the above equipments are known in the art and therefore they are not described in detail. The reforming section 110, in other embodiments of the invention, may comprise an autothermal reformer or a primary reformer followed by a secondary reformer.

The reforming section 110 is fed with a hydrocarbon-containing feedstock 1, such as natural gas. In the example, the natural gas enters the reformer 100 as a stream 3, after mixing with a stream 12 containing recycled carbon dioxide. The reformed hot syngas 4 produced in the primary reformer 100 is cooled in the gas cooler 101, e.g. from around 800° C. to 100° C. or less, and fed to the loop 103 through the compressor 102. Stream 5 indicates the output of cooler 101, the stream 6 is the inlet of compressor 102, and the stream 7 is the hi-pressure compressed make-up syngas fed to the loop 103.

The loop 103 operates usually around 100 bar, producing crude methanol 8. Said crude methanol 8 is a mixture of methanol and water, plus some $CO_2$ (typically around 1.5%) and is sent to a distillation section (not shown) to obtain methanol of a given purity or grade.

A low-pressure flash gas separator 104 separates the crude methanol stream 8 into a flash gas 9 and de-gassed crude methanol 19. The crude methanol 8 is de-pressurized through a valve (not shown), down to the working pressure of the separator 104, for example at around 5-10 bar, preferably 6 bar. The methanol stream 19 is sent to the downstream distillation section.

The flash gas 9, containing the carbon dioxide formerly dissolved in the crude methanol 8, is recycled to the reforming section 110. A stream 10 of light ends produced in the distillation section, in the example, is also recycled to said reforming section 110.

Referring with greater detail to the layout of FIG. 1, the reforming section 110 is equipped with a conventional $CO_2$-recovery section 105 and related compressor 106, recycling the carbon dioxide contained in the flue gas 11 of the reformer 100. The recovery section 105 delivers a $CO_2$-rich stream 14, obtained from said flue gas 11, to inlet of the compressor 106. Said compressor 106 delivers a stream 12, which is mixed with the feedstock 1, or with a portion 2 thereof as in FIG. 1, thus enriching of carbon dioxide the feed 3 of the reformer 100.

The flash gas 9 and light ends 10 are mixed to form a single stream 15, which is fed to the suction side of the compressor 106 and, hence, recycled to the primary reformer 100 in the same way as said $CO_2$-rich stream 14. In alternative embodiments, the streams 9 and 10 may be recycled to the reforming section 110 with separate flow lines.

Both the streams 9 and 10 contain a relevant amount of carbon oxides, mainly carbon dioxide. As an example, a typical composition of the flash gas 9 is around 60% $CO_2$, around 25% $CH_4$ and 10% hydrogen, with small percentages of nitrogen (2%), steam (2%), carbon oxide (<1%), plus small amounts (<0.01%) of He, Ar, methanol. The light ends 10 may contain for example 75% $CO_2$, 20% steam, some methanol and methane, plus inerts and impurities.

In the shown embodiment, the plant also comprises a hydrogen recovery section 107 for recovering $H_2$ from a purge gas stream 16 taken from the loop 103. Said section 107 outputs a hydrogen-rich stream 17 which is mixed with the output 5 of the gas cooler 101, to form the inlet flow 6 of the gas compressor 102. It should be noted that hydrogen is a reactant for the synthesis of methanol as seen in reactions (I) and (II) above, hence the recycle of the stream 17 is useful for the whole efficiency of the plant. A preferred injection point, as shown, is between the gas cooler 101 and the syngas compressor 102, at the suction side of said compressor.

The section 107 also produces a fuel stream 18 containing carbon oxides, which is recycled to the reformer 100, possibly mixed with a portion 13 of the feedstock 1. The remaining portion 2 of said feedstock 1, in this example, is mixed with the $CO_2$-containing stream 12 delivered by the compressor 106, to form the feed 3 of the reformer 100. The entity of the mixing portion 13 depends on specific needs, and may be for example around 30% of total feed 1.

Figure 2:
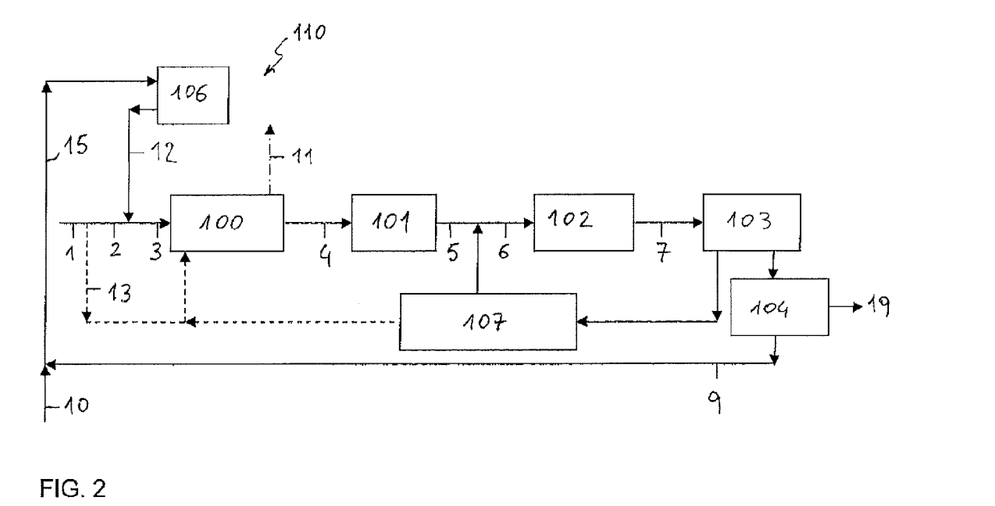
FIG. 2 is a simplified block diagram of a plant according to another embodiment of the invention.

A simplified layout is shown in FIG. 2, where the reforming section 110 has no $CO_2$-recovery section, and the flue gas 11 is discharged. The input of the compressor 106 is then the stream 15 formed by the flash gas 9 and/or the light-ends 10. The other equipments are as in FIG. 1.

The invention, as stated above, is applicable also to the revamping of existing plants. In this case, the invention is best applicable to a methanol plant featuring the $CO_2$ recovery from the reformer flue gas, as in FIG. 1. Assuming that the methanol plant already comprises the section 105 and compressor 106, the revamping is carried out basically by re-routing the piping of the flash gas 9 and/or light ends 10 to the suction side of the compressor 106. Usually, the compressor does not need substantial modification to receive this additional input.

For example, the prior-art layout of FIG. 3 can be revamped to the inventive layout of FIG. 1, substantially by re-routing the piping of flash gas 9 and light ends 10 to the inlet side of the compressor 106. Hence, a preferred revamping in accordance with the invention comprises the step of re-routing the piping of a flash gas separated by de-pressurization of crude methanol from the synthesis loop, and re-routing the piping of a further $CO_2$-containing stream recovered from distillation of crude methanol, said re-routing being directed to a $CO_2$ compressor feeding the reforming section.

Nevertheless, the invention is also applicable to revamping of methanol plants with no $CO_2$ recover from the flue gas, as in FIG. 2. In this case, the revamping involves the installation of a new compressor 106.

The invention achieves the aims and purposes as stated above. As an example, it has been found that by recycling the flash gas 9 and light ends 10, up to 20% less $CO_2$ is required from the recovery section 105, for a given output of make-up syngas to the loop 103. Accordingly, a new plant according to FIG. 1 can be realized with savings around 20% in the cost of said section 105.

EXAMPLE

The following is a comparison between a conventional methanol plant with $CO_2$ recovery from flue gas 11, as in FIG. 3, and the inventive plant according to the layout of FIG. 1, Tables 1a to 1c relate to the conventional plant (FIG. 3) and Tables 2a to 2c relate to the plant of the invention. The comparison has been done considering to keep approximately the same final production.

The energy consumption of the plant can be calculated as the heat value of the feed 1 (on LHV basis) per metric ton (mt) of methanol produced. In this example, the energy consumption is decreased from 7.33 GCal/mt of the existing plant to 7.29 GCal/mt; moreover the tables 1 and 2 show that the flue gas temperature and flow rate at the stack are decreased, improving the plant efficiency and reducing the environmental impact. It can be calculated that the better efficiency of the primary reformer reduces the carbon dioxide emissions of more than 6500 tons/year.

In case the radiant box and/or the $CO_2$ recovery section are close to their maximum capability, the invention can be applied to increase the plant production up to 0.4/0.6% of the final methanol production.

The following tables 1a to 1c contain data of the base plant of FIG. 3.

TABLE 1a (base plant)

| Stream | | 1 | 2 | 3 | 4 | 5 | 6 | 7 |
|---|---|---|---|---|---|---|---|---|
| Vapour Fraction (mole) | | 1.00 | 1.00 | 1.00 | 1.00 | 0.85 | 0.86 | 1.00 |
| Temperature | ° C. | 15.0 | 192.5 | 198.1 | 870.0 | 82.0 | 81.3 | 147.9 |
| Pressure | bar | 16.01 | 23.71 | 23.71 | 19.71 | 16.51 | 16.51 | 96.47 |
| Molar Flow | kmole/hr | 4115.5 | 6816.1 | 7797.3 | 17243.0 | 14072.5 | 14434.6 | 12004.7 |
| Mass Flow | kg/hr | 68057.1 | 118261.6 | 160969.2 | 240367.3 | 183237.7 | 186369.1 | 142557.9 |
| Composition | % mol wet | | | | | | | |
| CO | | — | 0.027% | 0.024% | 13.311% | 16.309% | 15.916% | 19.138% |
| $CO_2$ | | 1.030% | 0.579% | 12.845% | 7.118% | 8.718% | 8.814% | 10.586% |
| $H_2$ | | 0.010% | 0.632% | 0.553% | 45.248% | 55.440% | 56.030% | 67.371% |
| $H_2O$ | | — | 57.874% | 50.823% | 32.621% | 17.449% | 17.017% | 0.233% |
| $CH_4$ | | 97.560% | 40.275% | 35.207% | 1.559% | 1.911% | 2.035% | 2.447% |
| Ethane | | 0.520% | 0.212% | 0.186% | — | — | — | — |
| Propane | | 0.080% | 0.033% | 0.029% | — | — | — | — |
| nButane | | 0.040% | 0.016% | 0.014% | — | — | — | — |
| nPentane | | 0.020% | 0.008% | 0.007% | — | — | — | — |
| $N_2$ | | 0.720% | 0.331% | 0.292% | 0.132% | 0.162% | 0.174% | 0.209% |
| $O_2$ | | — | — | — | — | — | — | — |
| He | | 0.020% | 0.009% | 0.008% | 0.004% | 0.004% | 0.005% | 0.006% |
| $CH_3OH$ | | — | 0.001% | 0.001% | — | — | — | — |
| Ar | | — | 0,002% | 0.013% | 0.006% | 0.007% | 0.009% | 0.010% |

TABLE 1b (base plant)

| Stream | | 8 | 9 | 10 | 11 | 12 | 13 | 14 |
|---|---|---|---|---|---|---|---|---|
| Vapour Fraction (mole) | | 0.03 | 1.00 | 0.81 | 1.00 | 1.00 | 1.00 | 1.00 |
| Temperature | ° C. | 42.1 | 49.5 | 63.3 | 136.6 | 233.0 | 15.0 | 40.0 |
| Pressure | bar | 6.00 | 4.41 | 5.41 | 0.97 | 26,51 | 16.01 | 1.26 |
| Molar Flow | kmole/hr | 4719.8 | 148.5 | 84.9 | 19349.2 | 981.2 | 1331.5 | 1024.0 |
| Mass Flow | kg/hr | 135319.7 | 4646.8 | 3215.0 | 534540.7 | 42707.6 | 22018.7 | 43480.3 |
| Composition | % mol wet | | | | | | | |

TABLE 1b-continued (base plant)

| Stream | 8 | 9 | 10 | 11 | 12 | 13 | 14 |
|---|---|---|---|---|---|---|---|
| CO | 0.021% | 0.641% | 0.023% | — | — | — | — |
| $CO_2$ | 3.214% | 58.728% | 74.215% | 9.284% | 98.049% | 1.030% | 93.959% |
| $H_2$ | 0.358% | 11.242% | 0.242% | — | — | 0.010% | — |
| $H_2O$ | 25.048% | 2.275% | 18.882% | 20.339% | 1.835% | — | 5.930% |
| $CH_4$ | 0.817% | 24.781% | 2.087% | — | — | 97.560% | — |
| Ethane | — | — | — | — | — | 0.520% | — |
| Propane | — | — | — | — | — | 0.080% | — |
| nButane | — | — | — | — | — | 0.040% | — |
| nPentane | — | — | — | — | — | 0.020% | — |
| $N_2$ | 0.072% | 2.176% | 0.188% | 67.913% | 0.021% | 0.720% | 0.020% |
| $O_2$ | — | 0.001% | — | 1.653% | 0.001% | — | 0.001% |
| He | 0.002% | 0.068% | — | 0.004% | — | 0.020% | — |
| $CH_3OH$ | 70.466% | 0.002% | 4.362% | — | — | — | — |
| Ar | 0.003% | 0.085% | — | 0.807% | 0.094% | — | 0.090% |

TABLE 1c (base plant)

| Stream | | 15 | 16 | 17 | 18 | 19 |
|---|---|---|---|---|---|---|
| V.F. (mole) | | 0.93 | 1.00 | 1.00 | 1.00 | 0.00 |
| Temperature | °C. | 51.9 | 43.5 | 50.0 | 50.0 | 44.0 |
| Pressure | bar | 4.41 | 93.57 | 35.01 | 35.01 | 6.00 |
| Molar Flow | kmole/hr | 233.5 | 659.1 | 362.1 | 297.0 | 4848.8 |
| Mass Flow | kg/hr | 7861.8 | 8293.0 | 3131.3 | 5161.7 | 135672.9 |
| Composition | % mol wet | | | | | |
| CO | | 0.416% | 2.071% | 0.641% | 3.815% | — |
| $CO_2$ | | 64.361% | 10.390% | 12.557% | 7.748% | 1.329% |
| $H_2$ | | 7.242% | 49.858% | 78.951% | 14.385% | 0.004% |
| $H_2O$ | | 8.316% | 0.157% | 0.251% | 0.042% | 30.035% |
| $CH_4$ | | 16.526% | 34.359% | 6.879% | 67.866% | 0.036% |
| Ethane | | — | — | — | — | — |
| Propane | | — | — | — | — | — |
| nButane | | — | — | — | — | — |
| nPentane | | — | — | — | — | — |
| $N_2$ | | 1.453% | 2.929% | 0.640% | 5.720% | 0.003% |
| $O_2$ | | 0.001% | 0.001% | — | 0.003% | — |
| He | | 0.043% | 0.085% | 0.029% | 0.153% | — |
| $CH_3OH$ | | 1.588% | — | — | — | 68.592% |
| Ar | | 0.054% | 0.150% | 0.052% | 0.269% | — |

The following table 2a to 2c contain data of the revamped plant.

TABLE 2a (revamped plant)

| Stream | | 1 | 2 | 3 | 4 | 5 | 6 | 7 |
|---|---|---|---|---|---|---|---|---|
| Vapour Fraction (mole) | | | 1.00 | 1.00 | 1.00 | 0.85 | 0.86 | 1.00 |
| Temperature | °C. | 15.0 | 193.0 | 198.9 | 870.0 | 82.0 | 81.3 | 147.9 |
| Pressure | bar | 16.01 | 23.71 | 23.71 | 19.71 | 16.51 | 16.51 | 96.47 |
| Molar Flow | kmole/hr | 4098.4 | 6812.4 | 7853.1 | 17243.2 | 14076.2 | 14458.7 | 12028.2 |
| Mass Flow | kg/hr | 67774.3 | 118236.4 | 161706.0 | 240250.6 | 183185.0 | 186372.8 | 142550.8 |
| Composition | % mol wet | | | | | | | |
| CO | | — | 0.027% | 0.035% | 13.295% | 16.286% | 15.871% | 19.079% |
| $CO_2$ | | 1.030% | 0.566% | 12.726% | 7.103% | 8.696% | 8.779% | 10.542% |
| $H_2$ | | 0.010% | 0.644% | 0.776% | 45.271% | 55.453% | 56.098% | 67.433% |
| $H_2O$ | | — | 58.468% | 50.950% | 32.604% | 17.449% | 16.994% | 0.233% |
| $CH_4$ | | 97.560% | 39.686% | 34.898% | 1.561% | 1.912% | 2.038% | 2.449% |
| Ethane | | 0.520% | 0.209% | 0.182% | — | — | — | — |
| Propane | | 0.080% | 0.032% | 0.028% | — | — | — | — |
| nButane | | 0.040% | 0.016% | 0.014% | — | — | — | — |
| nPentane | | 0.020% | 0.008% | 0.007% | — | — | — | — |
| $N_2$ | | 0.720% | 0.332% | 0.343% | 0.156% | 0.191% | 0.206% | 0.247% |
| $O_2$ | | — | — | — | — | — | — | — |
| He | | 0.020% | 0.009% | 0.010% | 0.004% | 0.005% | 0.006% | 0.007% |
| $CH_3OH$ | | — | 0.001% | 0.019% | — | — | — | — |
| Ar | | — | 0.002% | 0.013% | 0.006% | 0.007% | 0.008% | 0.010% |

TABLE 2b (revamped plant)

| Stream | | 8 | 9 | 10 | 11 | 12 | 13 | 14 |
|---|---|---|---|---|---|---|---|---|
| Vapour Fraction (mole) | | 0.03 | 1.00 | 0.81 | 1.00 | 1.00 | 1.00 | 1.00 |
| Temperature | °C | 42.2 | 49.5 | 63.3 | 133.7 | 234.3 | 15.0 | 40.0 |
| Pressure | bar | 6.00 | 4.41 | 5.41 | 0.97 | 26.51 | 16.01 | 1.26 |
| Molar Flow | kmole/hr | 4718.7 | 141.8 | 84.9 | 18986.7 | 1040.7 | 1356.4 | 870.0 |
| Mass Flow | kg/hr | 135138.2 | 4373.9 | 3215.0 | 522389.0 | 43469.6 | 22430.5 | 36941.3 |
| Composition | % mol wet | | | | | | | |
| CO | | 0.020% | 0.643% | 0.023% | — | 0.089% | — | — |
| $CO_2$ | | 3.051% | 57.301% | 74.215% | 8.598% | 92.321% | 1.030% | 93.959% |
| $H_2$ | | 0.362% | 11.886% | 0.242% | — | 1.639% | 0.010% | — |
| $H_2O$ | | 25.155% | 2.262% | 18.882% | 20.380% | 1.743% | — | 5.930% |
| $CH_4$ | | 0.792% | 25.109% | 2.087% | — | 3.558% | 97.560% | — |
| Ethane | | — | — | — | — | — | 0.520% | — |
| Propane | | — | — | — | — | — | 0.080% | — |
| nButane | | — | — | — | — | — | 0.040% | — |
| nPentane | | — | — | — | — | — | 0.020% | — |
| $N_2$ | | 0.083% | 2.628% | 0.188% | 68.535% | 0.412% | 0.720% | 0.020% |
| $O_2$ | | — | 0.001% | — | 1.668% | 0.001% | — | 0.001% |
| He | | 0.003% | 0.083% | — | 0.004% | 0.012% | 0.020% | — |
| $CH_3OH$ | | 70.532% | 0.002% | 4.362% | — | 0.136% | — | — |
| Ar | | 0.003% | 0.085% | — | 0.814% | 0.088% | — | 0.090% |

TABLE 2c (revamped plant)

| Stream | | 15 | 16 | 17 | 18 | 19 |
|---|---|---|---|---|---|---|
| V.F. (mole) | | 0.93 | 1.00 | 1.00 | 1.00 | 0.00 |
| Temperature | °C | 52.0 | 43.5 | 50.0 | 50.0 | 44.2 |
| Pressure | bar | 4.41 | 93.57 | 35.01 | 35.01 | 6.00 |
| Molar Flow | kmole/hr | 226.7 | 691.0 | 382.5 | 308.5 | 4854.5 |
| Mass Flow | kg/hr | 7588.9 | 8536.5 | 3187.8 | 5348.7 | 135764.3 |
| Composition | % mol wet | | | | | |
| CO | | 0.411% | 1.999% | 0.614% | 3.716% | — |
| $CO_2$ | | 63.636% | 9.871% | 11.842% | 7.428% | 1.292% |
| $H_2$ | | 7.525% | 50.772% | 79.805% | 14.782% | 0.005% |
| $H_2O$ | | 8.487% | 0.156% | 0.249% | 0.042% | 30.102% |
| $CH_4$ | | 16.485% | 33.552% | 6.668% | 66.877% | 0.036% |
| Ethane | | — | — | — | — | — |
| Propane | | — | — | — | — | — |
| nButane | | — | — | — | — | — |
| nPentane | | — | — | — | — | — |
| $N_2$ | | 1.714% | 3.402% | 0.738% | 6.705% | 0.004% |
| $O_2$ | | 0.001% | 0.001% | — | 0.003% | — |
| He | | 0.052% | 0.101% | 0.035% | 0.184% | — |
| $CH_3OH$ | | 1.635% | — | — | — | 68.560% |
| Ar | | 0.053% | 0.145% | 0.050% | 0.263% | — |

The invention claimed is:

1. A process for producing methanol, comprising the steps of:
  a. reforming a hydrocarbon feedstock in a reforming process step, obtaining a make-up syngas comprising carbon oxides and hydrogen;
  b. reacting said make-up syngas in a methanol synthesis loop, obtaining crude methanol;
  c. processing said crude methanol to obtain methanol of a required purity;
  d. recovering at least one $CO_2$-rich stream from the processing of said crude methanol, and
  e. recycling said at least one $CO_2$-rich stream as an input stream for said reforming process step,
  wherein said step d) of recovering a $CO_2$-rich stream from the crude methanol comprises the recovering of a flash gas stream released by de-pressurization of the crude methanol and/or comprises the recovering of a gas stream containing carbon dioxide released by the crude methanol in a distillation process.

2. The process according to claim 1, where said step d) of recovering a $CO_2$-rich stream from the crude methanol comprises both the recovering of said flash gas stream released by de-pressurization of the crude methanol and the recovering of a light-ends gas stream containing carbon dioxide released by the crude methanol in a distillation process,
  wherein said flash gas stream and said light-ends stream are mixed together in a single $CO_2$-containing flow, forming said input stream recycled to reforming.

3. The process according to claim 1, where said $CO_2$-rich stream is compressed in a suitable $CO_2$ compressor and mixed with a hydrocarbon feed at the inlet of a reformer of said reforming section.

4. The process according to claim 1, where:
  a first carbon-dioxide containing stream is recovered from flue gas of reforming;
  said first stream is recycled to a reforming section via a $CO_2$ compressor; and
  said at least one $CO_2$-rich stream recovered from said crude methanol is fed to the suction side of said compressor, and recycled to the reforming section together with said first stream.

5. The process according to claim 1, further comprising the steps of:
  recovering a purge gas from the methanol synthesis loop;
  obtaining a hydrogen-rich stream and a fuel stream from processing of said purge gas;
  recycling said hydrogen-rich stream to the synthesis loop; and
  recycling said fuel stream to the reforming section.

6. A method for revamping of an existing plant for producing methanol, said existing plant comprising at least:
  a reforming section receiving a hydrocarbon feedstock, and producing a reformed make-up syngas comprising carbon oxides and hydrogen;
  a methanol synthesis loop, fed with the make-up syngas and producing crude methanol;
  a section where said crude methanol is processed to obtain methanol of a required purity;

means for recovering at least one $CO_2$-rich stream separated from processing said crude methanol, and means feeding said $CO_2$-rich stream to said reforming section, wherein the provision of said means for recovering a $CO_2$-rich stream, and feeding said stream to the reforming section, comprises the step of re-routing of a flash gas separated by de-pressurization of crude methanol from the synthesis loop, and/or re-routing of a $CO_2$-containing stream recovered from distillation of crude methanol, said re-routing being directed to a $CO_2$ compressor feeding the reforming section.

7. The method according to claim 6, further comprising the step of providing a compressor for the recovered $CO_2$-rich stream.

* * * * *